US010765458B2

(12) United States Patent
George et al.

(10) Patent No.: US 10,765,458 B2
(45) Date of Patent: *Sep. 8, 2020

(54) COUPLING DEVICES AND METHODS OF USING THE SAME

(71) Applicant: GLOBUS MEDICAL, INC., Audubon, PA (US)

(72) Inventors: Milan George, Collegeville, PA (US); Katherine Manninen, Limerick, PA (US)

(73) Assignee: Globus Medical Inc., Audubon, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/157,560

(22) Filed: Oct. 11, 2018

(65) Prior Publication Data

US 2019/0099204 A1    Apr. 4, 2019

Related U.S. Application Data

(63) Continuation of application No. 15/181,450, filed on Jun. 14, 2016, now Pat. No. 10,123,824, which is a (Continued)

(51) Int. Cl.
*A61B 17/70* (2006.01)
*A61B 17/56* (2006.01)
(Continued)

(52) U.S. Cl.
CPC ...... *A61B 17/7044* (2013.01); *A61B 17/0642* (2013.01); *A61B 17/56* (2013.01);
(Continued)

(58) Field of Classification Search
CPC .............. A61B 17/56; A61B 2017/564; A61B 17/7001; A61B 17/7002; A61B 17/7044;
(Continued)

(56) References Cited

U.S. PATENT DOCUMENTS 5,330,473 A   7/1994 Howland
6,136,002 A *  10/2000 Shih ................... A61B 17/7044
                                                    606/250

(Continued)

FOREIGN PATENT DOCUMENTS

JP    62100325    6/1987
JP    8308855     11/1996

*Primary Examiner* — Larry E Waggle, Jr.

(57) ABSTRACT

In one embodiment, a medical device includes an elongate member, a first coupler, and a second coupler. The elongate member has a first end portion, a second end portion, and a side portion. The side portion of the elongate member has a first receiving portion and a second receiving portion. The first receiving portion is configured to receive a first support member. The second receiving portion is configured to receive a second support member. The first coupler is coupled to the elongate member and is configured to engage the first support member to help retain the first support member within the first receiving portion. The second coupler is coupled to the elongate member and is configured to engage the second support member to help retain the second support member within the second receiving portion.

19 Claims, 16 Drawing Sheets

Related U.S. Application Data continuation of application No. 14/638,193, filed on Mar. 4, 2015, now Pat. No. 9,387,012, which is a continuation of application No. 13/352,711, filed on Jan. 18, 2012, now Pat. No. 8,998,956, which is a continuation-in-part of application No. 13/183,681, filed on Jul. 15, 2011, now Pat. No. 9,649,136.

(51) Int. Cl.
| | | |
|---|---|---|
| *A61B 17/88* | (2006.01) | |
| *A61B 17/064* | (2006.01) | |
| *A61B 17/80* | (2006.01) | |

(52) U.S. Cl.
CPC ...... *A61B 17/7001* (2013.01); *A61B 17/7002* (2013.01); *A61B 17/705* (2013.01); *A61B 17/7041* (2013.01); *A61B 17/7059* (2013.01); *A61B 17/809* (2013.01); *A61B 17/8033* (2013.01); *A61B 17/88* (2013.01); *A61B 2017/564* (2013.01); *Y10T 29/49826* (2015.01)

(58) Field of Classification Search
CPC ... A61B 17/7059; A61B 17/807; A61B 17/88; A61B 17/809
See application file for complete search history.

(56) References Cited

U.S. PATENT DOCUMENTS

| | | | | |
|---|---|---|---|---|
| 6,689,134 | B2* | 2/2004 | Ralph | A61B 17/8023 606/287 |
| 7,094,238 | B2* | 8/2006 | Morrison | A61B 17/7059 606/280 |
| 10,123,824 | B2* | 11/2018 | George | A61B 17/0642 |
| 2004/0162558 | A1* | 8/2004 | Hegde | A61B 17/7044 606/287 |

* cited by examiner

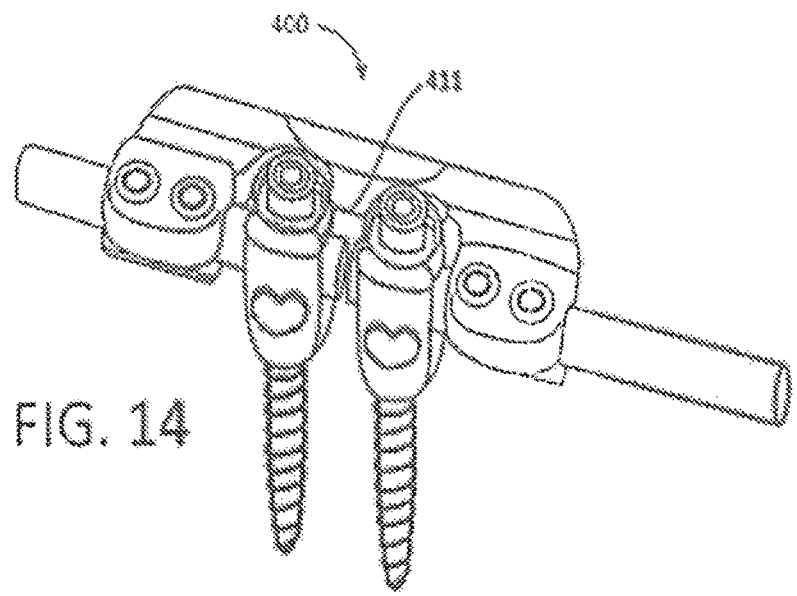
FIG. 14
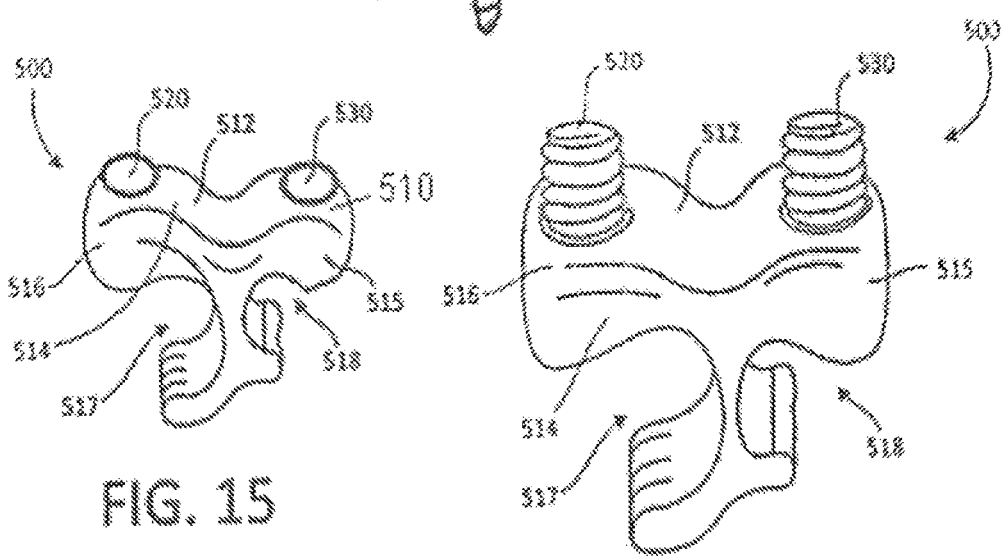
FIG. 15
FIG. 16
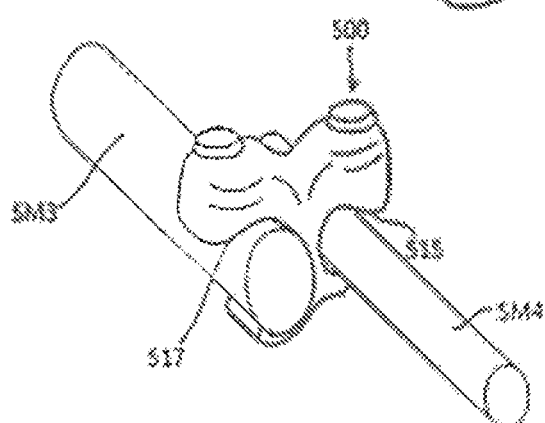
FIG. 17

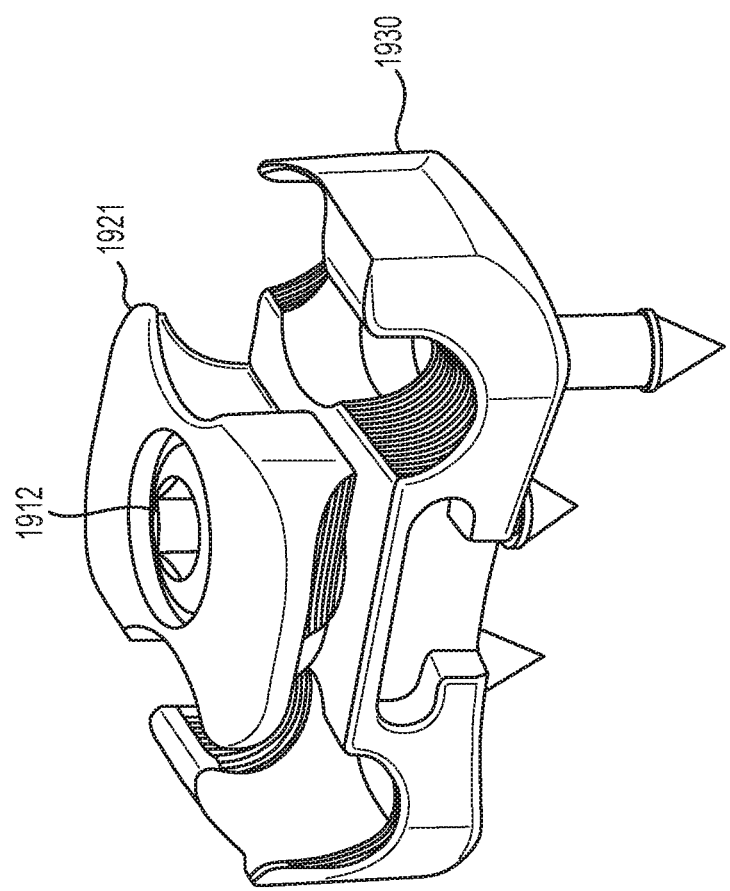

COUPLING DEVICES AND METHODS OF USING THE SAME

CROSS-REFERENCE TO RELATED APPLICATIONS

This Patent Application is a continuation of U.S. patent application Ser. No. 15/181,450, filed on Jun. 14, 2016 (published as U.S. Patent Publication No. 2016/0317192), which is a continuation of U.S. patent application Ser. No. 14/638,193, filed Mar. 4, 2015 (now U.S. Pat. No. 9,387,012), which is a continuation of U.S. patent application Ser. No. 13/352,711, filed Jan. 18, 2012, (now U.S. Pat. No. 8,998,956), which is a continuation-in-part application of U.S. patent application Ser. No. 13/183,681, filed on Jul. 15, 2011 (now U.S. Pat. No. 9,649136), the entire contents of each of which are incorporated by reference herein in their entireties for all purposes.

TECHNICAL FIELD

This disclosure relates generally to medical devices and more particularly to coupling devices configured to couple a first portion of a medical support system to a second portion of a medical support system.

BACKGROUND

A variety of medical devices and medical device systems are implanted within bodies of patients to provide support to portions of the bodies of the patients. For example, some medical device systems are implanted and coupled to backbones or spines of patients and are configured to provide support to the spinal bone structure of the patient. Some medical device systems that are configured to provide support to the spinal bone structure of a patient include support members or rods that extend between various portions of the medical device system. For example, the support members or rods may extend between portions of the medical device system that are coupled to adjacent vertebrae to provide support to the spinal bone structure to promote healing of the bone structures and/or otherwise maintain alignment and spacing of the spinal bone structures.

After implantation, however, the support members or rods of the medical devices or medical device systems may become weakened or break. It then may be necessary to perform an additional medical procedure to replace or repair the broken or weakened support members or rods. Additionally, it may become necessary or desirable to couple various support members or rods together after the implantation of such medical device systems.

Accordingly, there is a need for a coupling device that allows various support members or rods to be coupled together. For example, there is a need for a coupling device that is configured to allow broken or weakened rods to be coupled together. Additionally, there is a need for a coupling device that is configured to allow broken or weakened rods to be coupled together without having to replace the support members or rods or perform a more difficult and time consuming procedure to bend or torque the rods to force the support members or rods to conform to the specific configuration of the coupling device. There is also a need for a coupling device that because of its size and profile avoids excessive tissue damage adjacent the surgical site.

SUMMARY

Systems, devices, and methods related to improved coupling mechanisms are provided. In some embodiments, an implantable system comprises a bottom member having one or more slots for receiving one or more rod members; a top member attachable to the bottom member; and a set screw insertable through both the top member and bottom member, wherein rotation of the set screw results in a secure locking of the system.

In other embodiments, an implantable system comprises a bottom member having a pair of slots for receiving two rod members; a top member attachable to the bottom, whereby in a first open orientation, the top member does not obscure openings of the pair of slots, while in a second closed orientation, the top member does obscure openings of the pair of slots; and a set screw insertable through both the top member and bottom member.

In other embodiments, an implantable system comprises a bottom member having one or more slots for receiving rod members; a top member attachable to the bottom member, the top member including an upper portion and a lower portion insertable into an aperture formed in the bottom member; and a set screw insertable through both the top member and bottom member.

BRIEF DESCRIPTION OF THE DRAWINGS

FIG. 14 is a perspective view of a medical device coupled to a medical device system.

FIGS. 15 and 16 are perspective views of a medical device according to an embodiment of the invention.

FIG. 17 is a perspective view of the medical device of FIGS. 15 and 16 coupled to a medical device system.

FIG. 41 is a top perspective view of an alternative staple stabilizations system according to some embodiments of the present application.

DETAILED DESCRIPTION

The devices and methods described herein are generally directed to procedures for coupling portions of bodily implants together within a body of a patient. In some embodiments, the implants are configured to provide support to a portion of the body of the patient. For example, in some embodiments, the devices and methods described herein are configured to provide support to a spine or back of a patient. In other embodiments, other portions of the body of the patient are supported by the devices.

Figure 1:
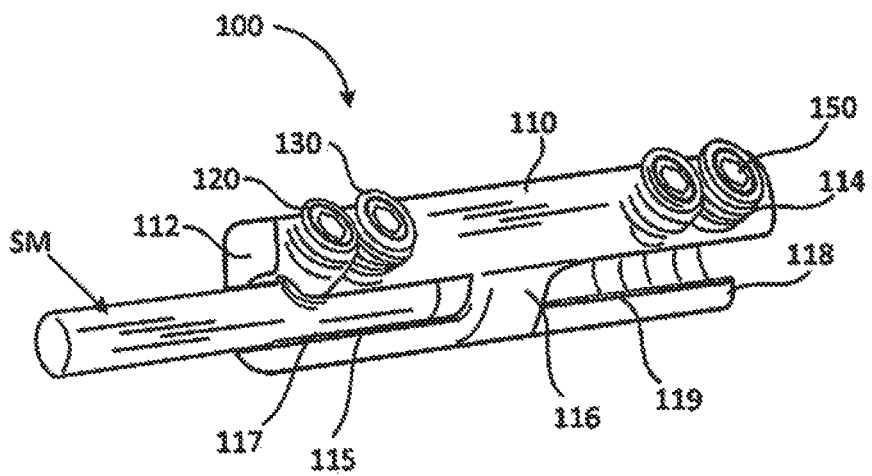
FIGS. 1 and 2 are perspective views of a medical device according to an embodiment of the invention.
Figure 2:
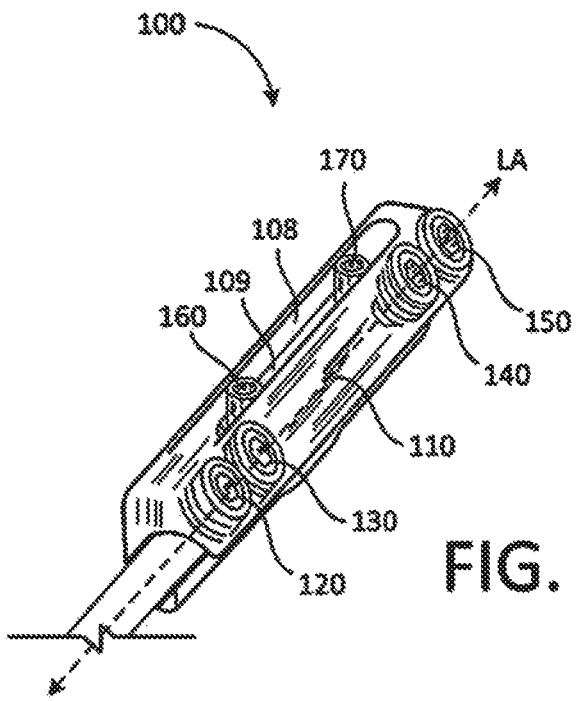
Figure 3:
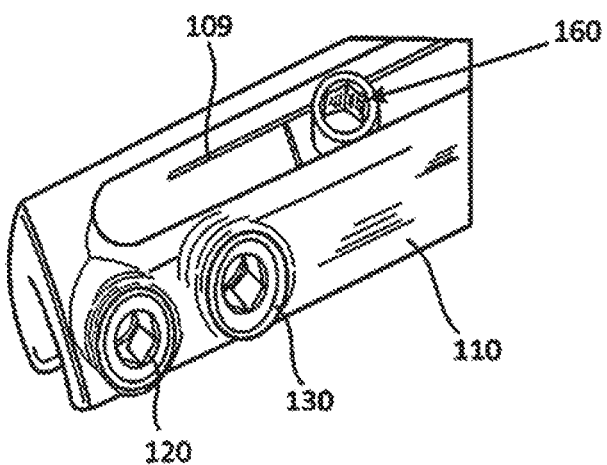
FIG. 3 is a perspective view of a portion of the medical device of FIGS. 1 and 2.

FIGS. 1 and 2 are perspective views of an apparatus or medical device 100 according to an embodiment of the invention. FIG. 3 is a perspective view of a portion of the apparatus or medical device 100. The apparatus or medical device 100 is configured to be coupled to portions of a medical device system to provide support to the medical device system. In the illustrated embodiment, the medical device 100 is configured to be coupled to a first support member SM and a second support member (not illustrated) of a medical device system. For example, in the illustrated embodiment, the medical device 100 is configured to be coupled to support members or rods of a spinal implant.

The apparatus or medical device 100 includes an elongate member 110, couplers 120, 130, 140, and 150 of a first type, and couplers 160 and 170 of a second type. The elongate member 110 includes a first end portion 112, a second end portion 114, and a side portion 116. The first end portion 112 is disposed opposite the second end portion 114. The side portion 116 extends from the first end portion 112 to the second end portion 114.

The side portion 116 defines a first receiving portion 117 and a second receiving portion 118. The first receiving portion 117 is configured to receive and house a first support member SM or rod of a medical device system (such as a spinal implant system). In the illustrated embodiment, first receiving portion 117 is configured to receive and house a portion of the first support member SM (and a portion of the first support member SM extends from the elongate member 100). The second receiving portion 118 is configured to receive and house a second support member of the medical device system or a portion of the second support member of the medical device system.

In the illustrated embodiment, the first receiving portion 117 and the second receiving portion 118 each include a cavity and an opening, such as an elongate opening that is in communication with the cavity. The first support member SM may be inserted into or otherwise coupled to the elongate member 110 by moving the first support member SM through the opening and into the cavity of the first receiving portion 117 of the side portion 116. Similarly, in the illustrated embodiment, the second support member SM may be inserted into or otherwise coupled to the elongate member 110 by moving the second support member through the opening and into the cavity of the second receiving portion 118 of the side portion 116.

In some embodiments, the first support member SM is coupled to a first portion of the medical device system and the second support member is coupled to a second portion of the medical device system. The apparatus 100 may be used to couple the first support member to the second support member to operatively couple the first portion of the medical device system to the second portion of the medical device system. In some embodiments, the first portion of the medical device system is a bone screw that is coupled to a first vertebrae and the second portion of the medical device system is a bone screw that is coupled to a second vertebrae. In some embodiments, the first support member SM and the second support member may be portions of a support member that broke into the first support member SM and the second support member. In such embodiments, the apparatus 100 or coupling device may be used to recouple the first support member SM to the second support member to repair the broken support member.

In some embodiments, the first receiving portion 117 and the second receiving portion 118 each include a sloped or ramped surface. The sloped or ramped surfaces are configured to help retain the support members within the receiving portions 117 and 118. For example, in some embodiments, the sloped or ramped surfaces are configured to help retain the support members within the receiving portions 117 and 118 via a frictional fit. In some embodiments, the lower surfaces 115 and 119 include sloped or ramped surfaces to help retain the support members within the receiving portions 117 and 118.

In the illustrated embodiment, the elongate member 110 is generally tubular in shape and has a relatively low profile. In other words, the cross-sectional sectional shape of the elongate member 110 (taken along a line generally perpendicular to the longitudinal axis LA of the elongate member) is generally circular. The diameter of the elongate member is relatively small to allow the apparatus 100 to avoid unnecessary disruption of the tissue surrounding the surgical site. Although the cross-sectional shape of the elongate member 110 is generally circular in the illustrated embodiment, in other embodiments, the elongate member has a different cross-sectional shape. For example, in some embodiments, the elongate member has an oval, rectangle, or any other cross-sectional shape.

In some embodiments, the first receiving portion 117 and the second receiving portion 118 are configured to receive and house support members of the same sizes, dimensions, or shapes. For example, in some embodiments, the first receiving portion 117 and the second receiving portion 118 are of the same size or include openings and cavities of the same size. In other embodiments, the first receiving portion 117 is configured to receive and house a support member of a first size, dimension, or shape and the second receiving portion 118 is configured to receive and house a support member of a second size, dimension, or shape different than the first size, dimension, or shape. For example, in some embodiments, the first receiving portion 117 is of a first width (has an opening or a cavity of a first width) and the second receiving portion 118 has a second width (has an opening or a cavity of a second width) greater than the first width.

Couplers 120, 130, 140, and 150 are of similar construction and function. Accordingly, only the coupler 120 will be described in detail. The coupler 120 is coupled to the elongate member 110. The coupler 120 is configured to move from a first position to a second position to engage a support member that is disposed within the first receiving portion 117 to help retain the support member within the first receiving portion 117. In other words, the coupler 120 is configured to at least contribute to the retention (for example, during normal bodily conditions) of the support member within the first receiving portion 117. In some embodiments, the coupler 120 is configured to engage the support member such that the frictional fit of the support member within the first receiving portion 117 is increased. In other words, the coupler 120 is configured to apply a pressure to the support member to help retain the support member within the first receiving portion 117.

In other embodiments, the coupler 120 is configured to move from a first position while the support member is being inserted into the receiving portion to a second position after the support member is disposed within the receiving portion to provide a barrier (i.e., to partially close the opening) to help prevent the removal of the support member from the first receiving portion 117.

In the illustrated embodiment, coupler 120 includes a set screw. The set screw of the coupler 120 can be rotated with respect to the elongate member 110 to move the set screw of the coupler 120 from a first position with respect to the elongate member 110 to a second position with respect to the elongate member 110. When the set screw of the coupler 120 is in its second position a portion of the set screw extends into the first receiving portion 117 and is configured to contact or engage the support member SM disposed within the first receiving portion 117 (as best illustrated in FIG. 1) to help retain the support member within the first receiving portion 117.

Couplers 120, 130, 140, and 150 are longitudinally offset from each other. In other words, the couplers 120, 130, 140, and 150 are offset from each other along an axis parallel to the longitudinal axis LA of the support member 110. Couplers 120 and 130 are disposed such that they are configured to contact or engage the support member SM that is disposed within the first receiving portion 117. Couplers 140 and 150 are disposed such that they are configured to contact or engage a support member that is disposed within the second receiving portion 118.

Couplers 160 and 170 are structurally and functionally similar. Accordingly, only coupler 160 will be discussed in detail. Coupler 160 is coupled to the elongate member 110 and is configured to engage the first support member SM once the support member SM is disposed within the first receiving portion 117. Specifically, the coupler 160 is configured to move from a first position to a second position to engage a support member that is disposed within the first receiving portion 117 to help retain the support member within the first receiving portion 117. In some embodiments, the coupler 160 is configured to engage the support member such that the frictional fit of the support member within the first receiving portion 117 is increased. In other words, the coupler 160 is configured to apply a pressure to the support member to help retain the support member within the first receiving portion 117.

Coupler 160 is configured to be disposed at different locations along an axis parallel to the longitudinal axis LA of the elongate member 110. In the illustrated embodiment, coupler 160 is slidably coupled within a slot 109 defined by the elongate member 110. In other embodiments, coupler 160 is configured to be removably coupled to the elongate member 110 at different locations along an axis parallel to the longitudinal axis LA of the elongate member 110. The ability of coupler 160 to slidably move within slot 109 allows coupler 160 to accommodate a variety of differently dimensioned support members as well as accommodate a variety of differently positioned support members.

In the illustrated embodiment, coupler 160 includes a screw portion and a cam member. Specifically, the coupler 160 includes a cam member that is configured to extend into the first receiving portion 117 (such as the cavity) to and engage or contact the support member to help retain the support member within the first receiving portion 117. The cam member may be moved into engagement and out of engagement with the support member by rotating the screw portion with respect to the elongate member 110. Accordingly, the support member may be inserted into the receiving portion 117 and appropriately positioned while the cam member does not extend into the receiving portion (or is in a location outside of engagement with the support member). Once the support member is inserted into the receiving portion, the screw member may be rotated with respect to the elongate member to cause the cam member to engage the support member and help retain the support member within the first receiving portion 117.

In the illustrated embodiment, coupler 170 is slidably disposed within slot or groove 108 that is defined by the elongate member 110. Slot 109 and slot 108 are disposed within the same plane. More specifically, slot 109 and slot 108 are offset along an axis that extends parallel to the longitudinal axis LA of the elongate member 110.

In some embodiments, the elongate member defines a single slot in which both coupler 170 and coupler 160 move or slide within.

In the illustrated embodiment, coupler 170 and coupler 160 are radially offset from the couplers 120, 130, 140, and 150.

The components of the medical device 100 may be made or formed of any biocompatible material. For example, the components of the medial device 100 may be formed of a biocompatible plastic or polymer or a biocompatible metal material.

In use, the medical device or coupler 100 may be used to couple various portions of a medical device system together. In one embodiment, the medical device 100 may be used to couple a first support member of a spinal implant to a second portion of the spinal implant.

The medical device 100 may be moved with respect to the first portion of the medical device system (such as a support member of the medical device system) to insert the first portion of the medical device system into the first receiving portion 117 of the medical device 100. As the receiving portion 117 is disposed on a side portion 116 of the elongate member 110, the first portion of the medical device may be moved laterally into the first receiving portion 117. In other words, an end-most portion of the first portion of the medical device system does not need to be inserted into the receiving portion first. Rather, the receiving portion 117 may laterally receive the first portion of the medical device system.

Coupler 120 and 130 may then be rotated to help retain the first portion of the medical device system within the first receiving portion 117. Coupler 160 may then be moved or slid along the elongate member 110 to a location appropriate to engage the first portion of the medical device system. Coupler 160 may then be rotated with respect to the elongate member 110 to cause a cam portion of the coupler 160 to engage the first portion of the medical device system to help retain the first portion of the medical device system within the first receiving portion 117.

The above process may be used to couple the medical device 100 to a second portion of the medical device system (such as a second support member of a spinal implant). Specifically, the above process may be used to couple the second portion of the medical device system within the second receiving portion 118.

FIGS. 4-9 illustrate another embodiment of an apparatus or medical device 200. The apparatus or medical device 200 includes an elongate member 210, couplers 220 and 230, and couplers 240 and 250. In the illustrated embodiment, couplers 220 and 230 are of a first type and couplers 240 and 250 are of a second type different than the first type.

The elongate member 210 includes a first end portion 212, a second end portion 214, and a side portion 216. The first end portion 212 is disposed opposite the second end portion 214. The side portion 216 extends from the first end portion 212 to the second end portion 214.

The side portion 216 defines a first receiving portion 217 and a second receiving portion 218. The first receiving portion 217 is configured to receive and house a first support member or rod of a medical device system (such as a spinal implant system). In the illustrated embodiment, first receiving portion 217 is configured to receive and house a portion of the first support member. The second receiving portion 218 is configured to receive and house a second support member of the medical device system or a portion of the second support member of the medical device system.

In the illustrated embodiment, the first receiving portion 217 and the second receiving portion 218 each include a cavity and an opening, such as an elongate opening that is in communication with the cavity. The first support member may be inserted into or otherwise coupled to the elongate member 210 by moving the first support member through the opening and into the cavity of the first receiving portion 217 of the side portion 216. Similarly, in the illustrated embodiment, the second support member may be inserted into or otherwise coupled to the elongate member 210 by moving the second support member through the opening and into the cavity of the second receiving portion 218 of the side portion 216.

Figure 7:
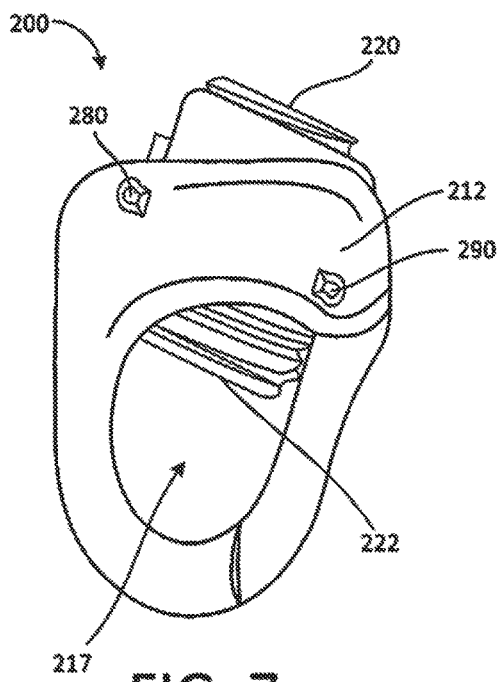
FIG. 7 is an end view of the medical device of FIG. 5.

Couplers 220 and 230 are of similar construction and function. Accordingly, only the coupler 220 will be described in detail. The coupler 220 is coupled to the elongate member 210. The coupler 220 is configured to move from a first position to a second position to engage a support member that is disposed within the first receiving portion 217 to help retain the support member within the first receiving portion 217. For example, as illustrated in FIG. 7, the coupler 220 includes a contact portion 222 that is configured to extend into the first receiving portion 217 and engage a support member disposed within the first receiving portion 217. In some embodiments, the coupler 220 is configured to engage the support member such that the frictional fit of the support member within the first receiving portion 217 is increased. In other words, the coupler 220 is configured to apply a pressure to the support member to help retain the support member within the first receiving portion 217.

In the illustrated embodiment, coupler 220 includes a set screw. The set screw of the coupler 220 can be rotated with respect to the elongate member 210 to move the set screw of the coupler 220 from its first position with respect to the elongate member 210 to its second position with respect to the elongate member 210. As best illustrated in FIG. 7, when the set screw of the coupler 220 is in its second position a portion (such as portion 222) of the set screw extends into the first receiving portion 217 and is configured to contact or engage the support member disposed within the first receiving portion 217 to help retain the support member within the first receiving portion 217.

Couplers 220 and 230 are laterally offset from each other along an axis parallel to a longitudinal axis of the support member 210. Coupler 220 is disposed such that it is configured to contact or engage a support member that is disposed within the first receiving portion 217. Coupler 230 is disposed such that it is configured to contact or engage a support member that is disposed within the second receiving portion 218.

Couplers 240 and 250 are structurally and functionally similar. Accordingly, only coupler 240 will be discussed in detail. Coupler 240 is coupled to the elongate member 210 and is configured to engage the first support member once the support member is disposed within the first receiving portion 217. Specifically, the coupler 240 is configured to move from a first position to a second position to engage a support member that is disposed within the first receiving portion 217 to help retain the support member within the first receiving portion 217. In some embodiments, the coupler 240 is configured to engage the support member such that the frictional fit of the support member within the first receiving portion 217 is increased. In other words, the coupler 240 is configured to apply a pressure to the support member to help retain the support member within the first receiving portion 217.

Coupler 240 is configured to be disposed at different locations along an axis parallel to the longitudinal axis of the elongate member 210. In the illustrated embodiment, coupler 240 is slidably coupled within a slot 209 defined by the elongate member 210. In other embodiments, coupler 240 is configured to be removably coupled to the elongate member 210 at different locations along an axis parallel to the longitudinal axis of the elongate member 210.

Figure 4:
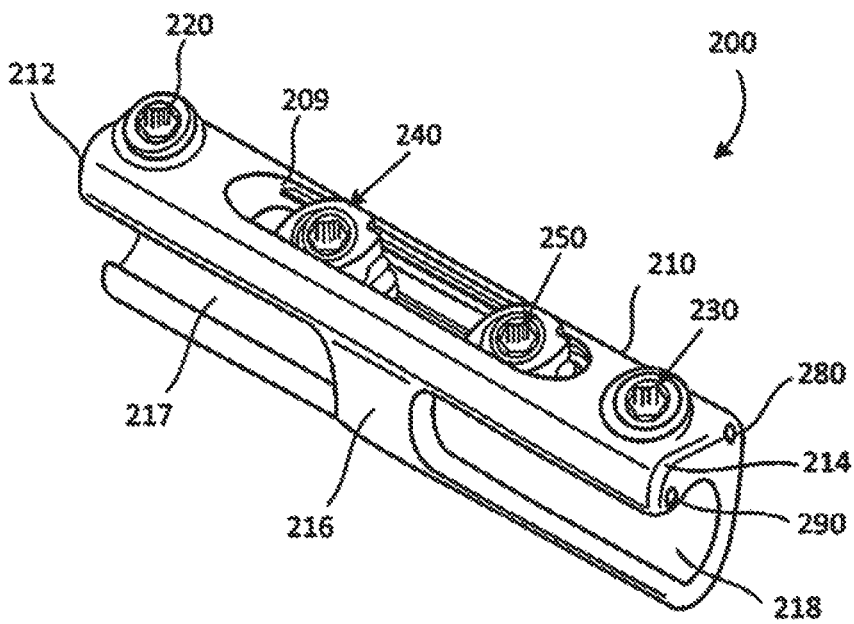
FIG. 4 is a perspective view of a medical device according to an embodiment of the invention.
Figure 5:
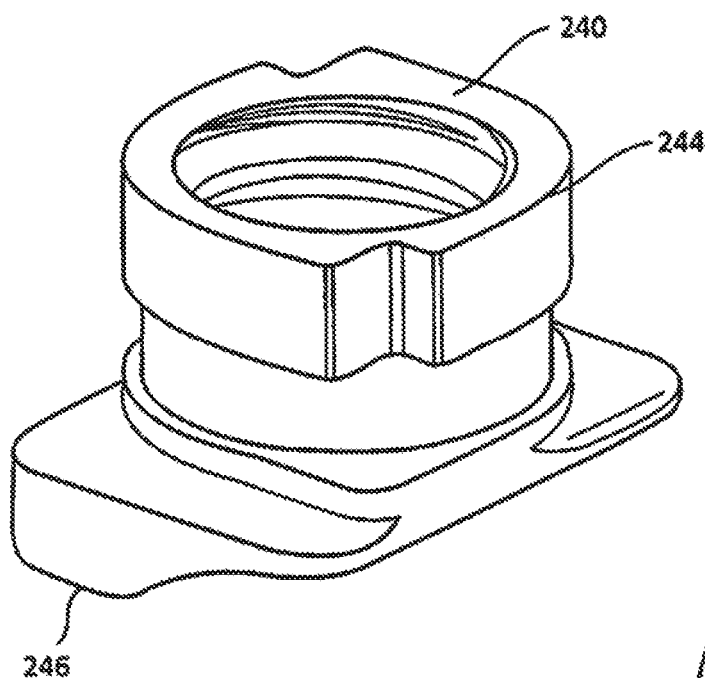
FIG. 5 is a perspective view of a coupler of a medical device according to an embodiment of the invention.
Figure 8:
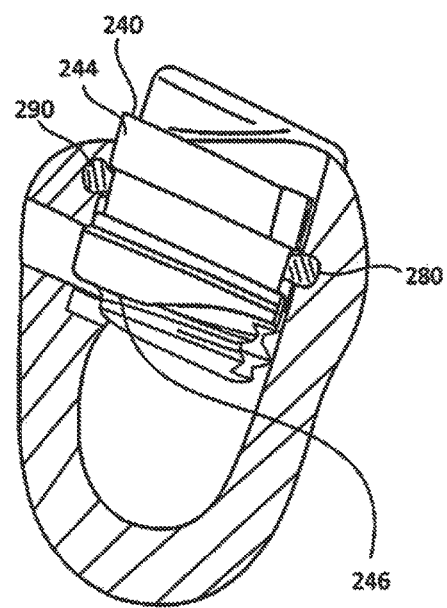
FIG. 8 is a cross-sectional view of the medical device of FIG. 5 taken along line A-A of FIG. 9.
Figure 9:
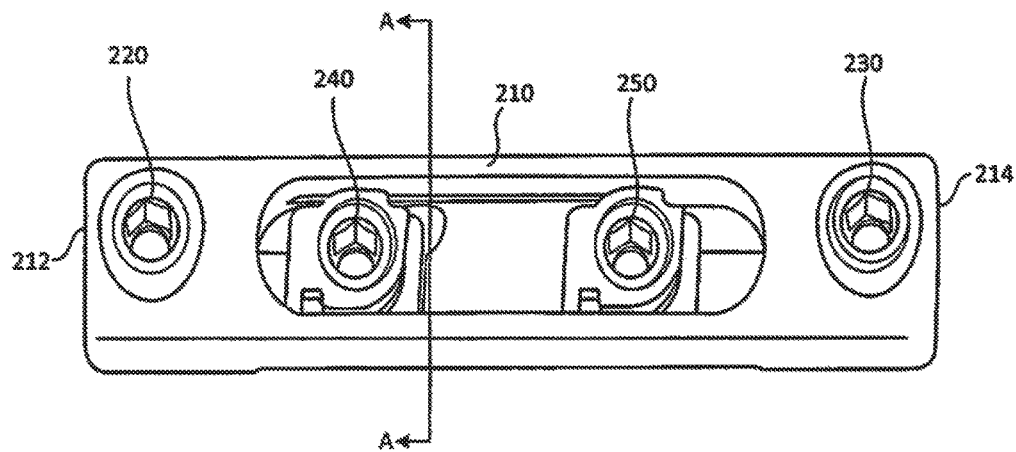
FIG. 9 is a top view of the medical device of FIG. 5.

As best illustrated in FIGS. 4, 7, and 8, the medical device 200 includes retention rods 280 and 290 that extend through at least a portion of the elongate member 210. The retention rods 280 and 290 extend along the slot 209 defined by the elongate member 210. The retention rods 280 and 290 are configured to engage the couplers 240 and 250 to help retain the couplers 240 and 250 within the slot 209. For example (as best illustrated in FIG. 8), in some embodiments, the couplers 240 and 250 are configured to slide along the retention rods 280 and 290.

In some embodiments, to slidably dispose the couplers 240 and 250 within the slot 209, the couplers 240 and 250 may be placed within slot 209 and then the retention rods 280 and 290 may be slid into the elongate member 210. The retention rods 280 and 290 may be slid into the elongate member 210 such that they engage a portion of the couplers 240 and 250 to slidably retain the couplers on the retention rods 280 and 290 and within the slot 209.

Figure 6:
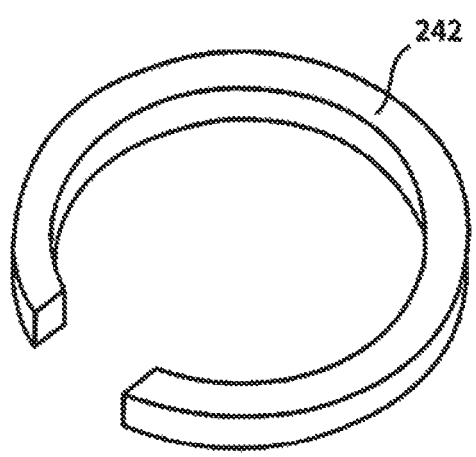
FIG. 6 is a perspective view of a ring of the coupler of FIG. 5.

In other embodiments, the couplers 240 and 250 may include a retention ring (such as retention ring 242 as illustrated in FIG. 6). The couplers 240 and 250 may be inserted into the slot 209 and the retention rings may be snapped or coupled to the couplers 240 and 250. The retention rings may then be disposed within slots or grooves defined by the elongate member 210 to slidably couple the couplers 240 and 250 within the slot 209.

In the illustrated embodiment, coupler 240 includes a screw portion 244 and a cam member 246. Specifically, the coupler 240 includes a cam member 246 that is configured to extend into the first receiving portion 217 and engage or contact the support member to help retain the support member within the first receiving portion 217. The cam member 246 may be moved into engagement and out of engagement with the support member by rotating the screw portion 244 with respect to the elongate member 210. Accordingly, the support member may be inserted into the receiving portion 217 while the cam member 246 does not extend into the receiving portion 217 (or is in a location outside of engagement with the support member). Once the support member is inserted into the receiving portion 217, the screw member 244 may be rotated with respect to the elongate member 210 to cause the cam member 246 to engage the support member and help retain the support member within the first receiving portion 217.

In the illustrated embodiment, coupler 240 and coupler 250 are longitudinally offset from the couplers 220 and 230.

Figure 10:
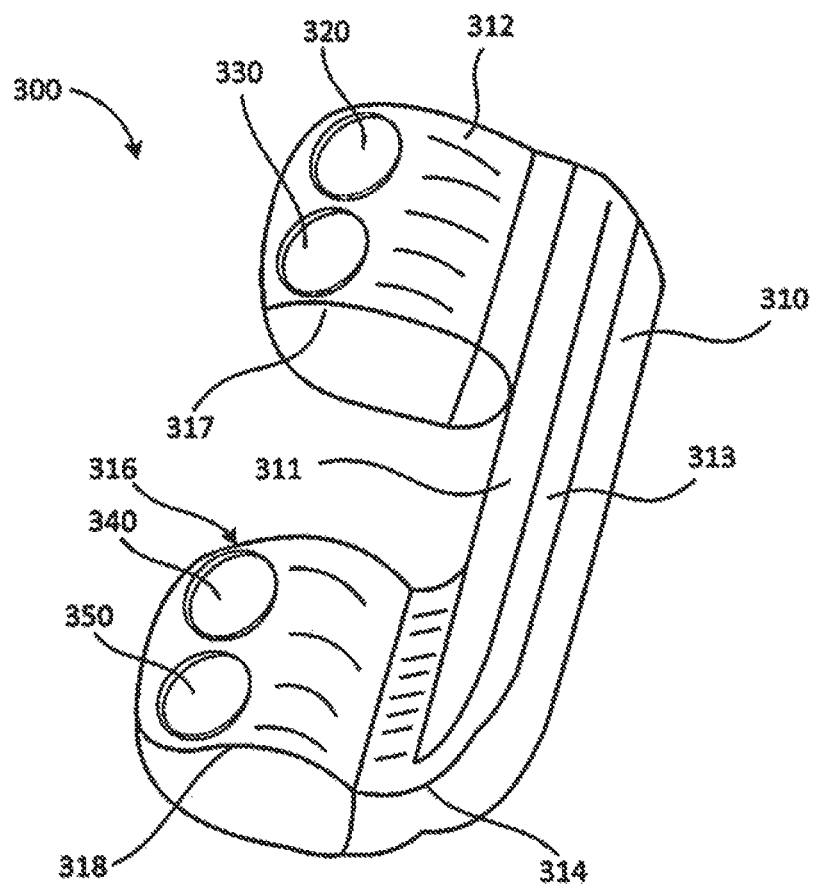
FIG. 10 is a perspective view of a medical device according to an embodiment of the invention.
Figure 11:
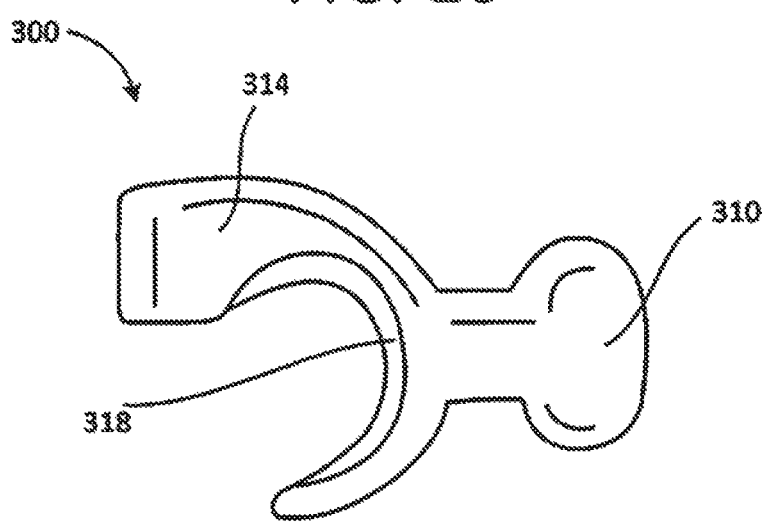
FIG. 11 is an end view of the medical device of FIG. 10.
Figure 12:
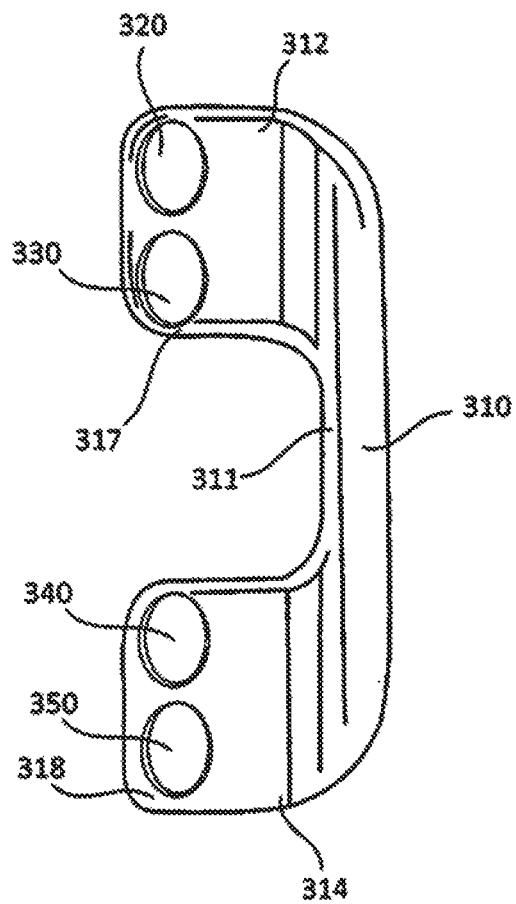
FIG. 12 is a top view of the medical device of FIG. 10.

FIGS. 10-12 illustrate another embodiment of an apparatus or medical device 300. The apparatus or medical device 300 is configured to couple two portions of a medical device system together. Specifically, the medical device 300 is configured to couple various portions of a broken support member or rod of a spinal implant. Such breaks of support members or rods may occur near the bone screws or bone anchors. The medical device 300 is configured to be coupled to the broken support members or rods at locations proximate the bone screws or bone anchors. In one example, medical device 300 may couple broken rods in an end to end or co axial orientation.

The medical device 300 includes an elongate member 310 and couplers 320, 330, 340, and 350. The elongate member 310 includes a first end portion 312, a second end portion 314, and a side portion 316. The side portion 316 defines a first receiving portion 317 and a second receiving portion 318.

The receiving portions 317 and 318 are configured to receive and house portions of a medical device system (such as support members or rods of a spinal implant). The couplers 320, 330, 340, and 350 are configured to move from first positions to second positions. In their first positions, the couplers 320, 330, 340, and 350 are configured to allow the portions of the medical device system to be inserted into the receiving portions 317 and 318. At their second positions, the couplers 320, 330, 340, and 350 are configured to contact or engage the support members or rods to help retain the support members within the receiving portions 317 and 318.

In the illustrated embodiment, the elongate member 310 includes a narrow or thin portion 313. In some embodiments, the narrow or thin portion 313 may be bent or curved to facilitate the coupling of the medical device 300 to various portions of a medical device system.

Figure 13:
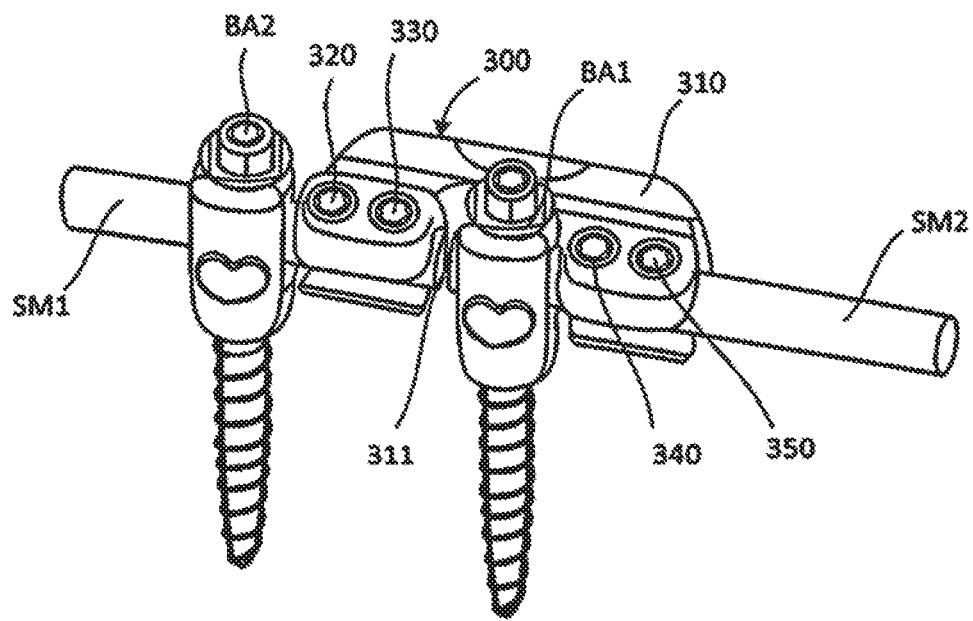
FIG. 13 is a perspective view of the medical device of FIG. 10 coupled to a medical device system.

FIG. 13 illustrates the medical device 300 coupled to portions of a medical device system MDS. The medical device system MDS includes a first support member SM1, a second support member SM2, a first bone anchor BA1, and a second bone anchor BA2. The medical device 300 is coupled to the first support member SM1 and to the second support member SM2. In the illustrated embodiment, the elongate member 310 defines an open portion 311. As best illustrated in FIG. 13, the open portion 311 of the elongate member 310 is configured to receive a bone screw or a bone anchor when the medical device is coupled to first support member SM1 and the second support member SM2 of the medical device system MDS.

As illustrated in FIG. 14, in another embodiment, a medical device 400 includes an elongated open portion 411. The open portion is configured to receive more than one bone screw or bone anchor.

FIGS. 15 and 16 illustrate an apparatus or medical device 500. The apparatus or medical device 500 may be used to couple various portions of a medical device system together. For example, the medical device 500 may be used to couple a first support member or rod and a second support member or rod of a spinal implant together. In some embodiments, the medical device 500 may be used to couple portions of a spinal implant that is currently in place within the body of a patient. In some embodiments, the use of the medical device 500 may provide a less disruptive surgery, decrease the time of surgery, or minimize the dissection area.

The medical device 500 includes an elongate member 510, a first coupler 512, and a second coupler 514. The elongate member 510 includes a first end portion 512, a second end portion 514 opposite the first end portion 512, a first side portion 516, and a second side portion 515 opposite the first side portion 516. In the illustrated embodiment, the first side portion 516 and the second side portion 515 each extend from the first end portion 512 to the second end portion 514.

The first side portion 516 defines a first receiving portion 517 and the second side portion 515 defines a second receiving portion 518. The receiving portions are configured to receive and house support members or rods of a spinal implant system. In the illustrated embodiment, the first receiving portion 517 is configured to receive a support member of a first size and the second receiving portion 518 is configured to receive a support member of a second size smaller than the first size. Thus, the medical device 500 may be used to couple a support member or rod of a first size to a support member or rod of a second, different size.

The coupling members 520 and 530 are screw members that may be placed in a first position (as illustrated in FIG. 15) to allow the support members to be placed or inserted into the receiving portions 517 and 518. The coupling members 520 and 530 may be placed in a second position (as illustrated in FIG. 16) to contact or engage the support members disposed in the receiving portions 517 and 518 to help retain the support members within the receiving portions 517 and 518.

FIG. 17 illustrates the medical device 500 coupled to a first support member SM3 and a second support member SM4. The first support member SM3 is disposed within the first receiving portion 517 and the second support member SM4 is disposed within the second receiving portion 518. The first support member SM3 is larger in diameter than the second support member SM4. FIG. 17 illustrates that the support members SM3 and SM4 are received in a substantially parallel orientation.

Figure 18:
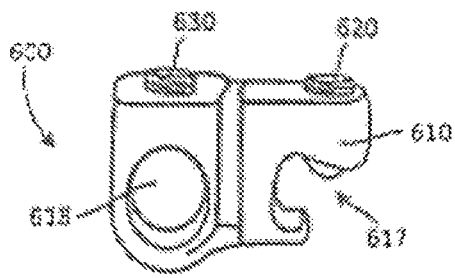
FIG. 18 is a perspective view of a medical device according to an embodiment of the invention.

FIG. 18 is a perspective view of an embodiment of a medical device 600. The medical device 600 includes an elongate member 610, a first coupler 620, and a second coupler 630. The elongate member 610 defines a first receiving portion 617 and a second receiving portion 618. The first receiving portion 617 has a C-shaped and may laterally receive a support member of a spinal implant. In other words, the first receiving portion 617 may receive a support member that is disposed at the side of medical device 600. The second receiving portion 618 is a lumen that includes a first end portion and opening and a second end portion and opening. The second receiving portion 618 is configured to receive a support member from an end portion of the elongate member 610 (through an end of the lumen).

Figure 19:
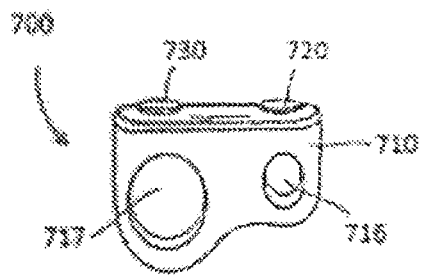
FIG. 19 is a perspective view of a medical device according to an embodiment of the invention.
Figure 20:
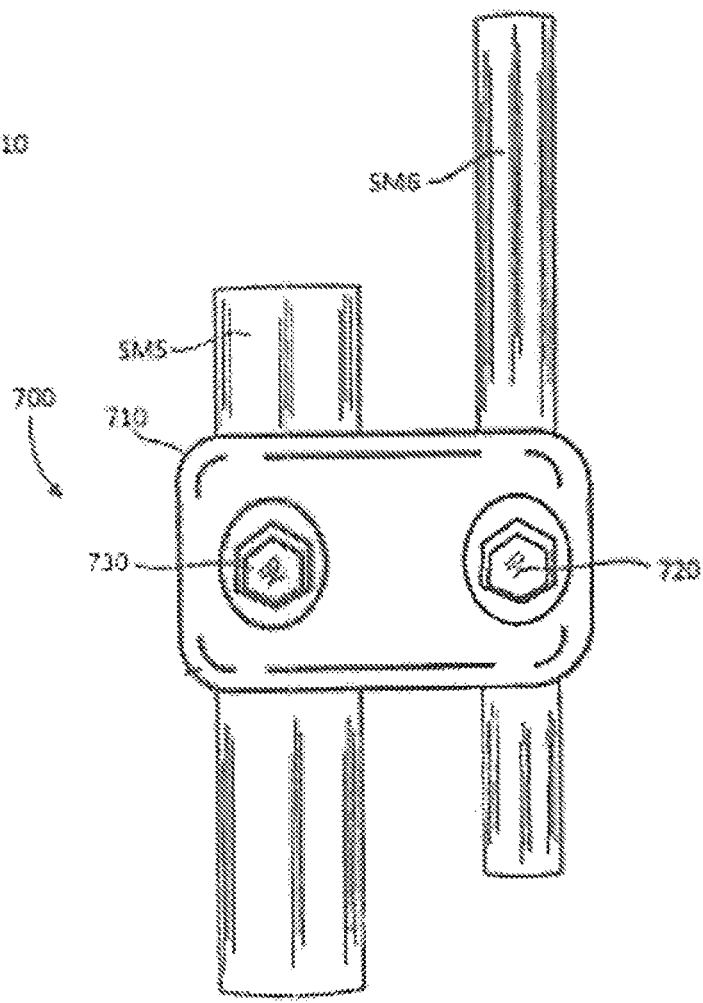
FIG. 20 is a top view of the medical device of FIG. 19 coupled to a medical device system.

FIG. 19 is a perspective view of an embodiment of a medical device 700. The medical device 700 includes an elongate member 710, a first coupler 720 and a second coupler 730. The elongate member 710 defines two receiving portions 716 and 717 that are lumens that are configured to receive support members from an end portion of the medical device 700. FIG. 20 illustrates the medial device 700 coupled to a first support member SM5 and a second support member SM6. The first support member SM5 is larger in diameter than the second support member SM6.

Figure 21:
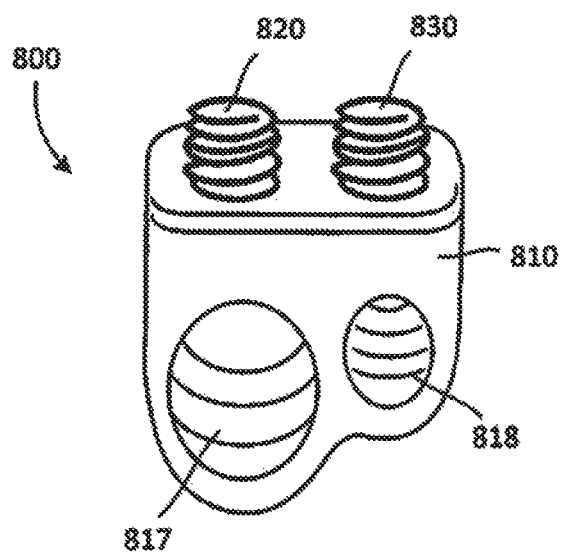
FIG. 21 is a perspective view of a medical device according to an embodiment of the invention.

FIG. 21 is a perspective view of an embodiment of a medical device 800. The medical device 800 includes an elongate member 810, a first coupler 820 and a second coupler 830. The elongate member 810 defines two receiving portions 817 and 818. The receiving portions 817 and 818 define lumens that are configured to receive support members from an end portion of the medical device 800.

Figure 22:
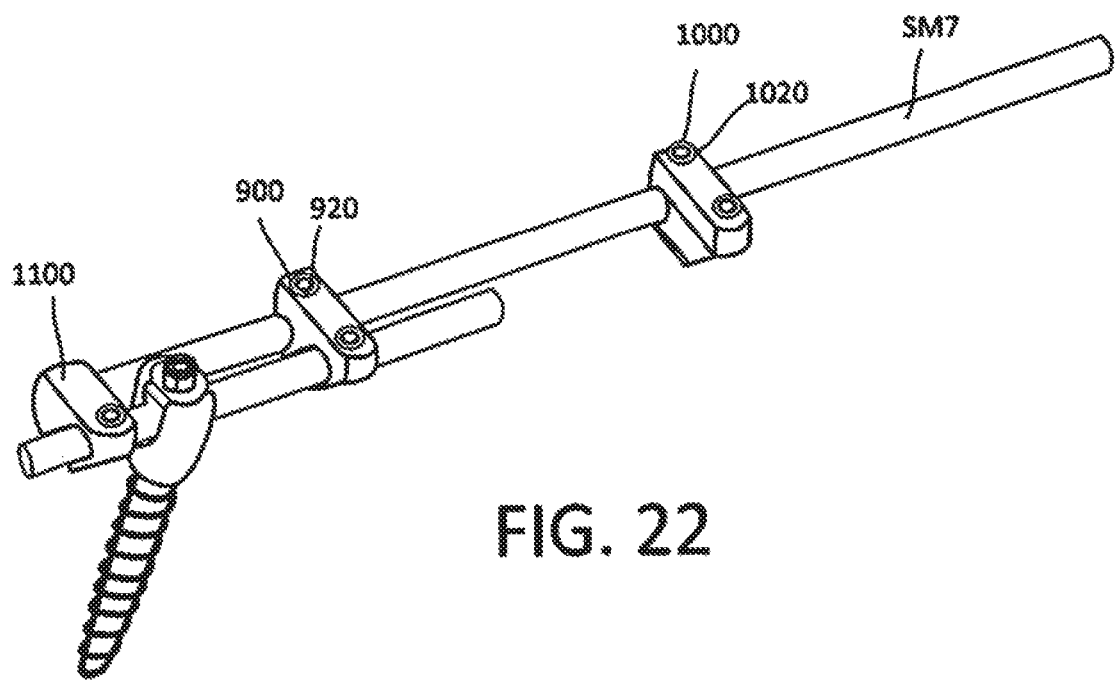
FIG. 22 is a perspective view of a medical device coupled to a medical device system.

FIG. 22 is a perspective view of medical devices 900 and 1000 coupled to a support member SM7. The medical devices 900 and 1000 are configured to move along the support member SM7. For example, the medical devices 900 and 1000 may be configured to slide along the support member SM7. Once placed in the correct location along the support member SM7, the couplers 920 and 1020 of the medical devices 900 and 1000, respectively, may be moved or screwed down to fixedly couple the medical devices 900 and 1000 to the support member SM7.

In some embodiments, the support member SM7 is prevented from rotating within the receiving portions of the medical devices 900 and 1000. For example, the receiving portions may have a shape, an engagement member, or other feature that helps prevent the support member SM7 from rotating within the receiving portions with respect to the medical devices 900 and 1000.

In the illustrated embodiment, the medical devices 900 and 1000 are configured to be coupled to a second support member. As illustrated, medical device 900 is coupled to a second support member SM8.

In the illustrated embodiment, a medical device 1100 is fixedly coupled to one end portion of the support member SM7. In other words, the medical device 1100 is not configured to move along the support member SM7.

FIGS. 23-26 are perspective views of various embodiments of medical devices 1200, 1300, 1400, and 1500. The medical devices 1200, 1300, 1400, and 1500 are configured to couple an end portion of a support member (such as a rod of a spinal implant) to an end portion of another support member. The medical devices 1200, 1300, 1400, and 1500 may be configured to be coupled to support members of different sizes.

Figure 23:
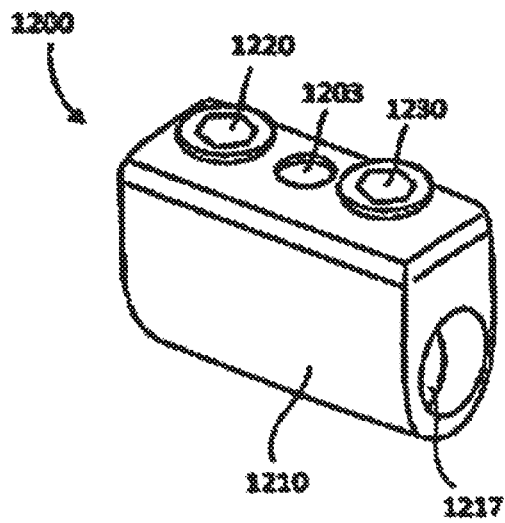
FIGS. 23-26 are perspective views of medical devices according to embodiments of the invention.

As illustrated in FIG. 23, the medical device 1200 includes an elongate member 1210, a first coupler 1220, and a second coupler 1230. The elongate member 1210 defines a first receiving portion 1217 configured to receive a first support member. The elongate member 1210 also defines a second receiving portion (not illustrated) configured to receive a second support member. The elongate member 1210 defines an opening or a window 1203 that is configured allow a user to view the support members (or a portion of the support members) once the support members are disposed within the first receiving portion 1217 and second receiving portion. In the illustrated embodiment, the opening or window 1203 is disposed on a top surface of the elongate member 1210. Specifically, the opening or window 1203 is disposed between the first coupler 1220 and the second coupler 1230 and is longitudinally offset from the first coupler 1220 and the second coupler 1230.

Figure 24:
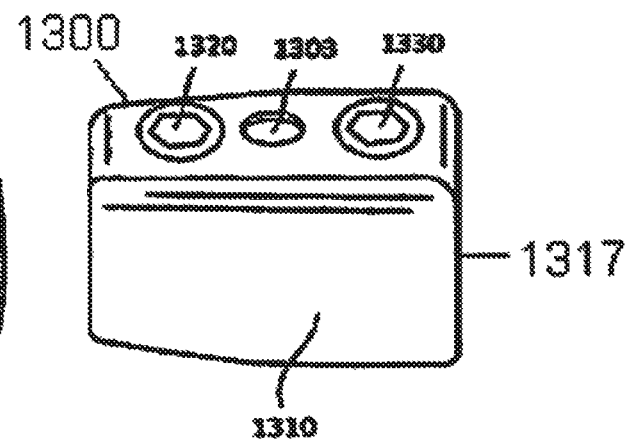

As illustrated in FIG. 24, the medical device 1300 includes an elongate member 1310, a first coupler 1320, and a second coupler 1330. The elongate member 1310 defines a first receiving portion 1317 configured to receive a first support member. The elongate member 1310 also defines a second receiving portion configured to receive a second support member. The elongate member 1310 defines an opening or a window 1303 that is configured allow a user to view the support members (or a portion of the support members) once the support members are disposed within the first receiving portion 1317 and second receiving portion. In the illustrated embodiment, the opening or window 1303 is disposed on a top surface of the elongate member 1310.

Figure 25:
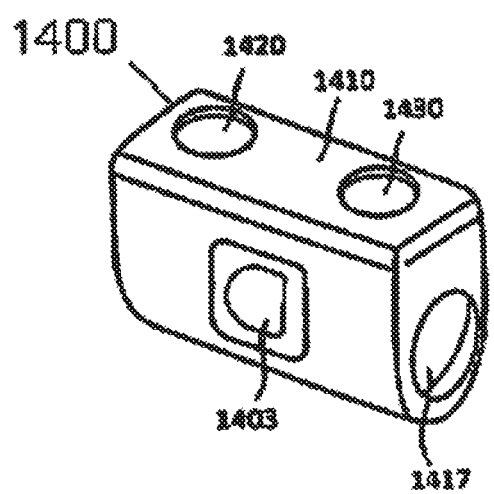

As illustrated in FIG. 25, the medical device 1400 includes an elongate member 1410, a first coupler 1420, and a second coupler 1430. The support member 1410 defines a first receiving portion 1417 configured to receive a first elongate member. The elongate member 1410 also defines a second receiving portion (not illustrated) configured to receive a second support member. The elongate member 1410 defines an opening or a window 1403 that is configured allow a user to view the support members (or a portion of the support members) once the support members are disposed within the first receiving portion 1417 and second receiving portion. In the illustrated embodiment, the opening or window 1403 is disposed on a side surface of the elongate member 1410 and is radially offset from the first coupler 1417 and the second coupler 1430.

Figure 26:
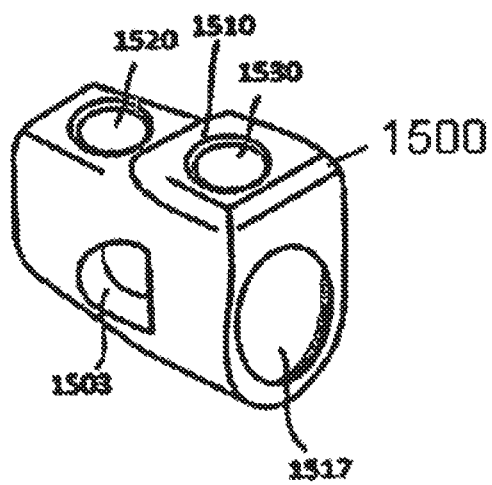

As illustrated in FIG. 26, the medical device 1500 includes an elongate member 1510, a first coupler 1520, and a second coupler 1530. The support member 1510 defines a first receiving portion 1517 configured to receive a first elongate member. The elongate member 1510 also defines a second receiving portion (not illustrated) configured to receive a second support member. The elongate member 1510 defines an opening or a window 1503 that is configured allow a user to view the support members (or a portion of the support members) once the support members are disposed within the first receiving portion 1517 and second receiving portion. In the illustrated embodiment, the opening or window 1503 is disposed on a side surface of the elongate member 1510.

Figure 27:
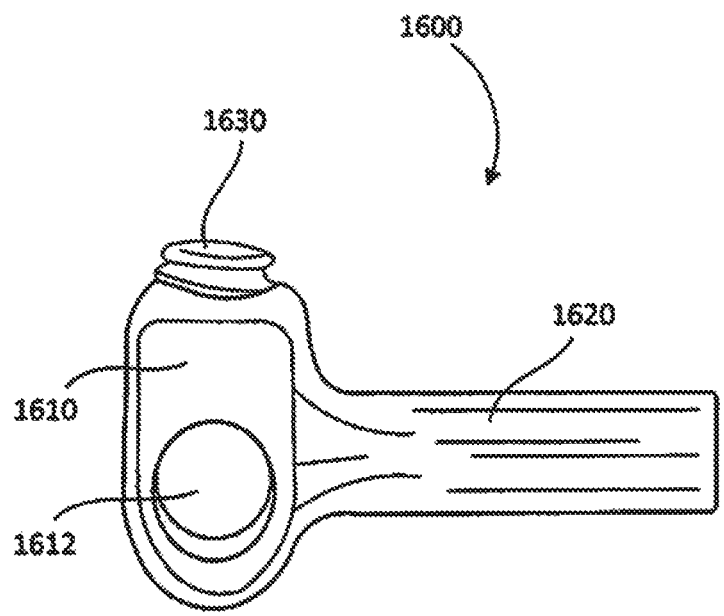
FIGS. 27 and 28 are side views of medical devices according to embodiments of the invention.
Figure 28:
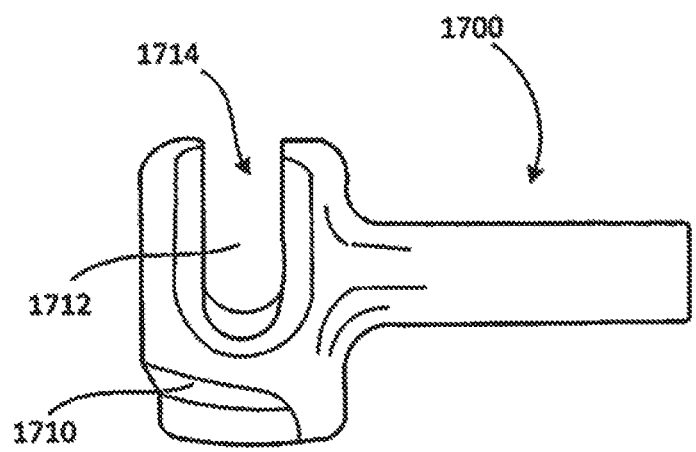

FIGS. 27 and 28 illustrate connectors that 1600 and 1700 are configured to connect a rod or support member to a support member or rod of a medical device system (such as a spinal implant). In some embodiments, the connectors 1600 and 1700 allow the support members to be coupled in an offset manner, decrease the time of surgery, and provide less disruptive options for surgery. Additionally, in some embodiments, the connectors 1600 and 1700 provide options for accommodating varying patient anatomy and may help lower morbidity rate in surgeries.

As illustrated in FIG. 27, connector 1600 includes a connector portion 1610 coupled to a support portion 1620. In some embodiments, the connector portion 1610 is integral or unitarily formed with the support portion 1620 which may be coupled to another component of a medical device system such as a bone screw. The connector portion 1610 defines a lumen 1612 that is configured to receive a support member of a medical device system. The connector 1600 also includes a set screw 1630 that is configured to engage a support member that is disposed within the lumen 1612 to help retain the support member within the lumen 1612.

As illustrated in FIG. 28, connector 1700 includes a connector portion 1710 that defines a cavity 1712 and an opening 1714 that communicates with the cavity 1712. Accordingly, a support member of a medical device system may be inserted into the cavity 1712 via the opening 1714.

Figure 29:
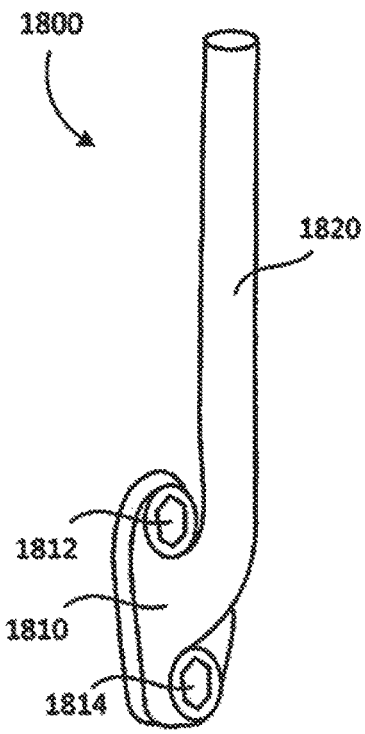
FIGS. 29 and 30 are perspective views of a medical device according to an embodiment of the invention.
Figure 30:
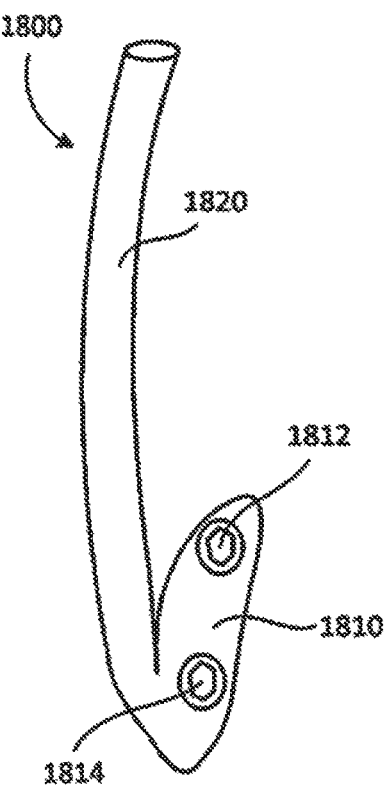
Figure 31:
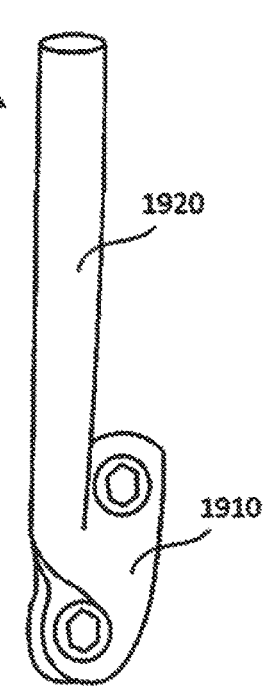
FIGS. 31 and 32 are perspective views of a medical device according to an embodiment of the invention.
Figure 32:
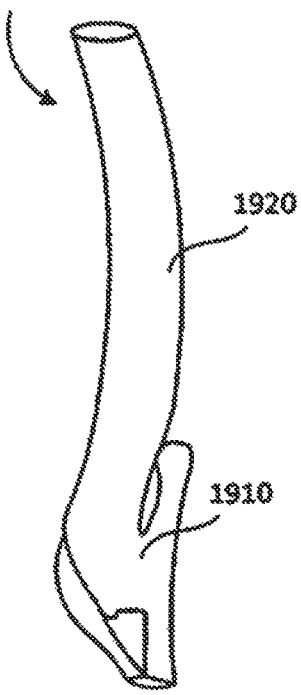

FIGS. 29 and 30 illustrate a medical device 1800 and FIGS. 31 and 32 illustrate a medical device 1900. The medical devices 1800 and 1900 are configured to be implanted into a body of a patient and provide support to a body or a portion of the body of the patient. For example, the medical devices 1800 and 1900 may be coupled to a spine of a patient to provide support to the spine of the patient or may be coupled to an existing spinal implant.

In some embodiments, the medical devices 1800 and 1900 include connection portions 1810 and 1910 and support rod portions 1820 and 1920 that are integral or unitarily formed. In some embodiments, integral or unitary construction provides a stronger medical device, reduces the number of fixation points of an implant, and reduces construction time. Rod portions 1820 and 1920 are configured and dimensioned to mate with other medical device systems or components such as device connectors or bone screws.

In some embodiments, the medical devices are formed of a stiff material such as a metal material. In some embodiments, the medical devices 1800 and 1900 are configured to align with the anatomical location of L5 pedicles. In such embodiments, the screws may be more easily placed. In other words, the devices 1800 and 1900 may not need to be bent in situ to align the screws.

In some embodiments, the medical devices 1800 and 1900 provide a platform for L5 reduction.

Figure 33:
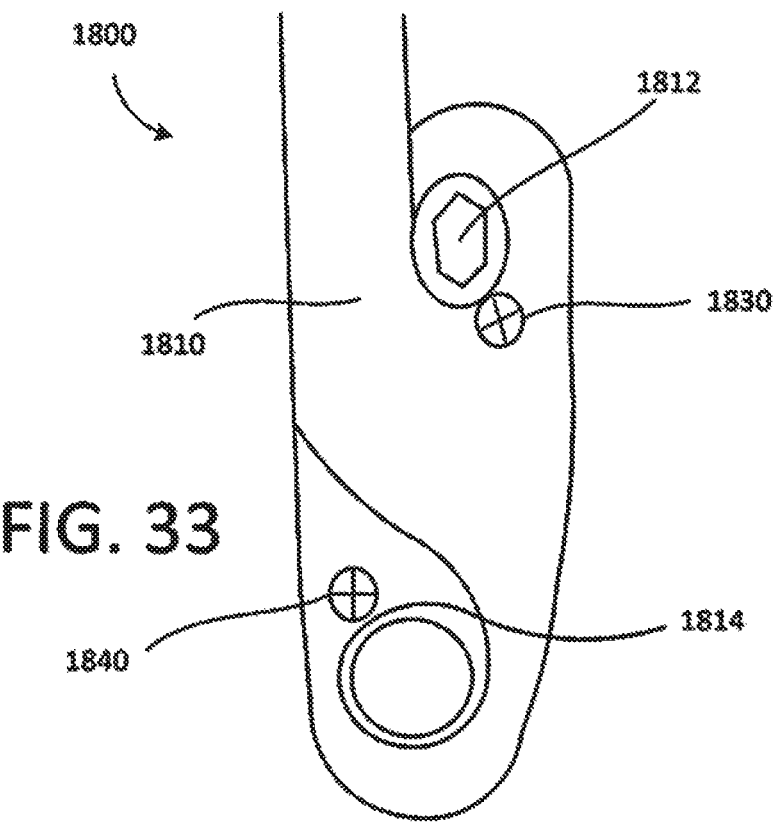
FIGS. 33 and 34 are side views of medical devices according to embodiments of the invention.

As illustrated in FIGS. 29 and 30, medical device 1800 includes a connection portion 1810 and a rod portion 1820. The connection portion 1810 defines openings 1812 and 1814. The openings 1812 and 1814 are configured to receive bone anchors or bone screws. As illustrated in FIG. 33, the bone anchors or bone screws may be retained within the openings 1812 and 1814 via a pair of couplers 1830 and 1840. In some embodiments, the couplers 1830 and 1840 are screws that are configured to engage the bone screws or bone anchors to help retain such bone anchors or bone screws within the openings 1812 and 1814.

Figure 34:
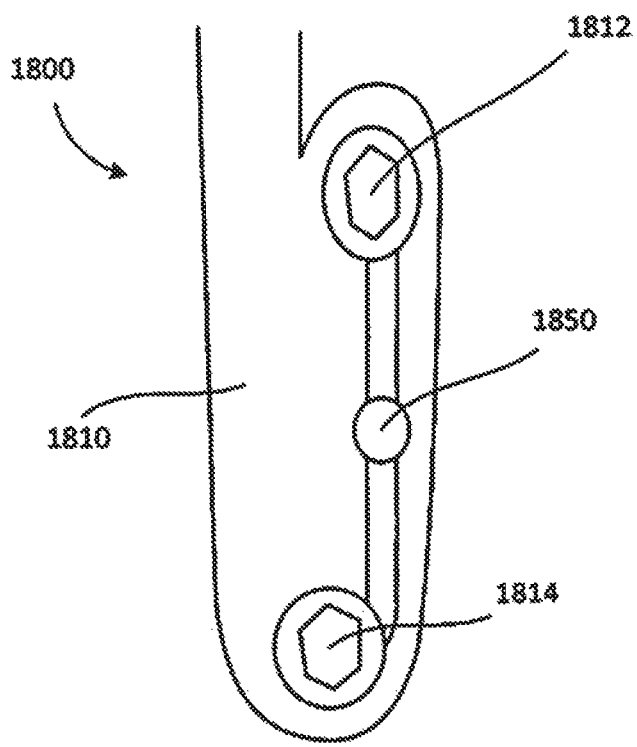

As illustrated in FIG. 34, in another embodiment, a cam member 1850 may be used to engage the bone anchors or bone screws to help retain the bone anchors or bone screws within the openings 1812 and 1814. For example, in some embodiments, the cam member 1850 maybe rotated from a position of disengagement (to allow the bone screws or bone anchors to be inserted into the openings 1812 and 1814) to a position of engagement (to help retain the bone screws or bone anchors within the openings 1812 and 1814).

As illustrated in FIGS. 31 and 32, the medical device 1900 includes a coupling portion 1910 and a rod portion 1920.

As best illustrated in FIG. 29, the rod portion 1820 curves to the right of the coupling portion 1810. As best illustrated in FIG. 31, the rod portion 1920 curves to the left of the coupling portion 1820.

Additional Embodiments

Additional embodiments of coupling systems and devices are now described. In particular, FIGS. 35-41 show different views of a novel staple stabilization system and individual components for attachment to one or more vertebral members. The staple stabilization system advantageously is of low profile, thereby helping to reduce the risk of tissue abrasion and damage in and around a surgical site.

Figure 35:
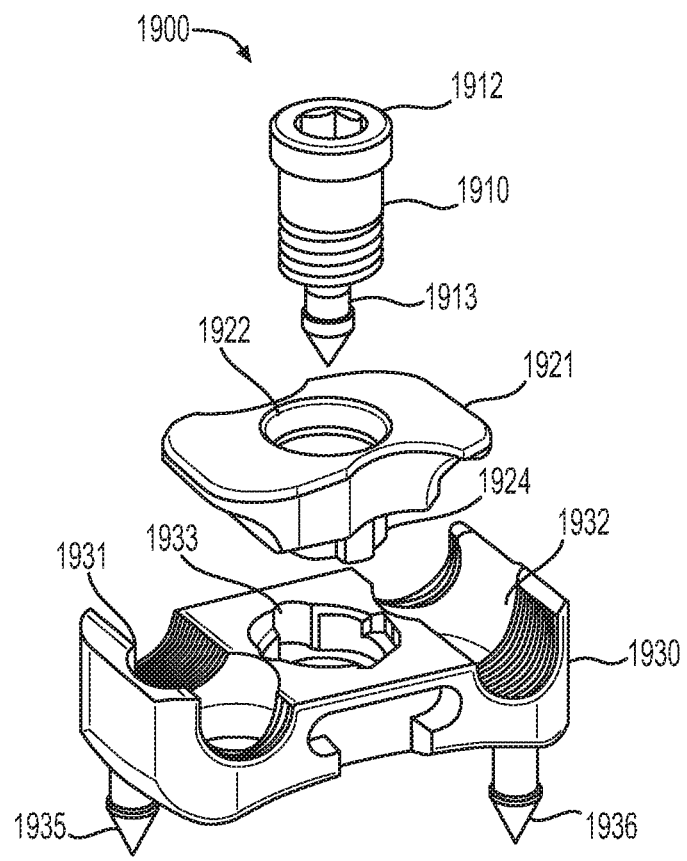
FIG. 35 is an exploded view of a staple stabilization system according to some embodiments of the present application.

FIG. 35 illustrates an exploded view of a staple stabilization system according to some embodiments of the present application. The staple stabilization system 2000 includes three low-profile components: a top member 1921 in the form of a top plate, a bottom member 1930 in the form of a bottom plate, and a set screw 2010.

Figure 37:
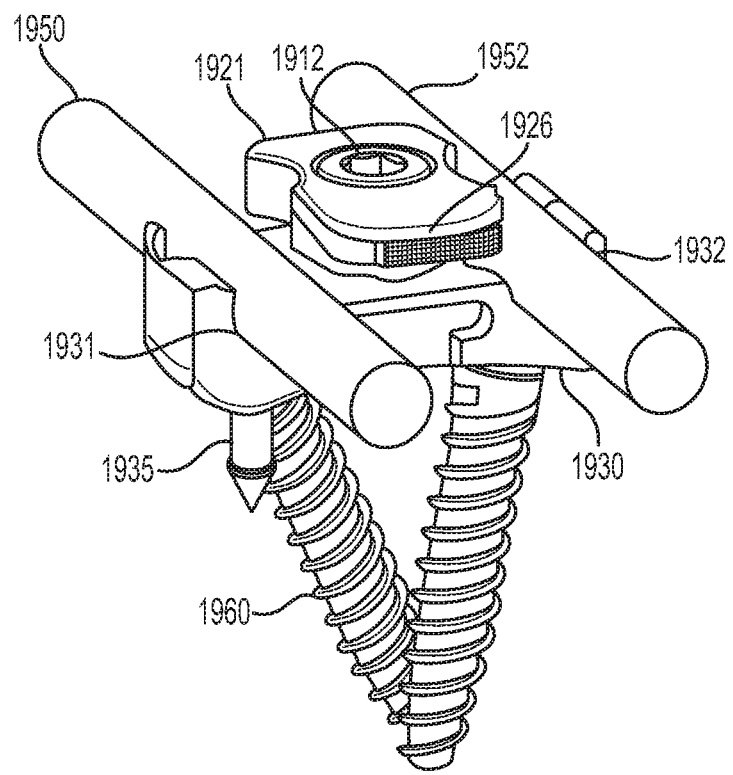
FIG. 37 is a top perspective view of a staple stabilization system having rod members with a top member in an open position according to some embodiments of the present application.
Figure 38:
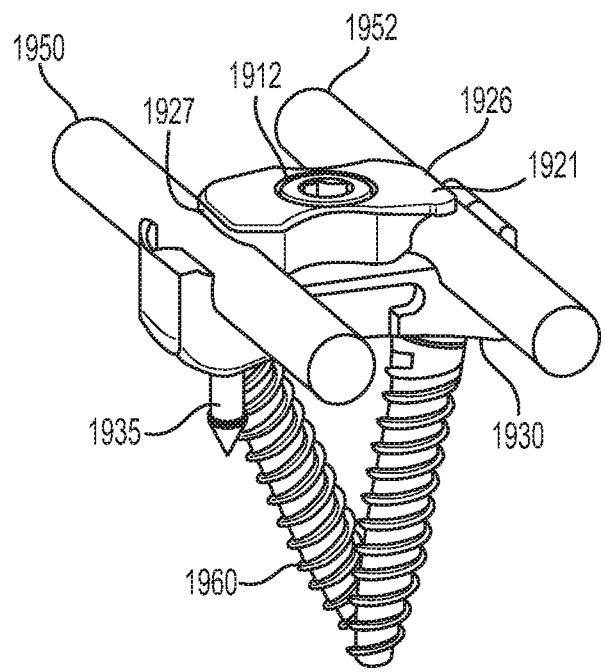
FIG. 38 is a top perspective view of a staple stabilization system having rod members with a top member in a closed position according to some embodiments of the present application.

The staple stabilization system 2000 is configured to receive and secure one or more rod members (as shown in FIGS. 37 and 38) for stabilization of the spine. When the system is in an "open" configuration, the staple stabilization system 2000 can receive rod members 1950, 1952 that rest within slots 1931, 1932 formed on the bottom member 1930, as shown in FIG. 37. In the open configuration, the top member 1921 is oriented such that its walls do not obstruct the openings of the slots 1931, 1932. Once the rod members 1950, 1950 are deposited in the slots 1931, 1932, the top member 1921 can be rotated and actuated into a "closed" position, whereby the rod members 1950, 1952 are securely held within the system, as shown in FIG. 38. To further secure the rod members 1950, 1952 within the system, the set screw 1912 can be rotated and tightened. Further details regarding the securing of the rod members 1950, 1950 to the system 2000 are discussed below.

As shown in FIG. 35, the bottom member 1930 is in the form of a plate having a pair of slots 1931, 1932 formed therein. The slots 1931 and 1932 are configured to receive rod members, as discussed above. The slots 1931 and 1932 include openings 1938 and 1939 (shown in FIGS. 39 and 40) that extend to a bottom surface of the bottom member 1930. The openings 1938 and 1939 are configured to receive one or more bone screws, such as bone screw 1960 in FIGS. 37 and 38, for securing the system to a vertebral body.

Figure 39:
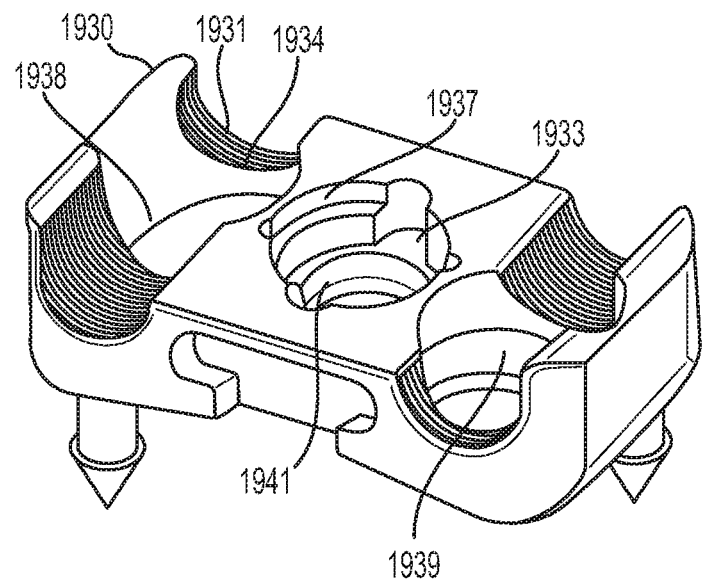
FIG. 39 is a top perspective view of a bottom member of a staple stabilization system according to some embodiments of the present application.

The bottom member 1930 further includes a middle opening 1933 in between the slots 1931 and 1932 that extends from a top surface to a bottom surface of the bottom member 1930. The middle opening 1933 of the bottom member 1930 is configured to receive a portion of the top member 1921 therein. The middle opening 1933 of the bottom member 1930 is also configured to have threads 1941 (as shown in FIG. 39) that can mate with threads of a set screw 2010 to secure the rod members within the system.

The bottom member 1930 further includes one or more protruding members or prongs 1935 and 1936 that can extend from a bottom surface of the bottom member 1930. In some embodiments, the protruding members 1935 and 1936 have pointed tips that can advantageously engage a surface of a vertebral body prior to inserting additional bone screws through the system. This way, the protruding members 1935, 1936 help to stabilize the system against a vertebral member even before the staple system is secured to the vertebral member.

As shown in FIG. 35, the top member 1921 is in the form of a plate member having an upper portion 2020 and a lower portion 1924. The lower portion 1924 is configured to be received within the opening 1933 of the bottom member 1930. In addition, an opening 1922 (shown in FIG. 35) for receiving a set screw 2010 is formed in the top member 1921 from a top surface to a bottom surface of the top member. While in some embodiments, the opening 1922 is substantially circular, in other embodiments, the opening 1922 is non-circular and can receive a set screw having a variety of different shapes.

As shown in FIG. 35, the set screw 1912 includes an upper screw portion 2012 and a lower screw portion 1913.

The upper screw portion 2012 can comprise a cylindrical body. In some embodiments, the upper screw portion 2012 includes one or more threads that can mate with a threaded portion of the top and/or bottom member, such as the threaded portion 1941 of the bottom member 1930 in FIG. 39. The lower screw portion 1913 can comprise a pointed distal tip that allows the set screw 1912 to engage with a vertebral body. After rod members are received within the system 2000, the set screw 1912 can be rotated to thereby secure the rod members therein.

Advantageously, rotation of the single set screw 1912 provides a locking mechanism for both of the rod members, thereby reducing the time needed to implant a dual rod construct within a body.

In some embodiments, the set screw 1912 can include a reverse single or dual outer diameter thread. If a surgeon desires to disassemble an assembled staple stabilization system by unscrewing the set screw 1912, the addition of the reverse thread can serve as a safety mechanism to limit the complete removal of the set screw from the system within a body of the patient. In some embodiments, if a top portion of the thread is modified, then fully backed up, the set screw and top member will rotate simultaneously, without the need of additional drivers.

Figure 36:
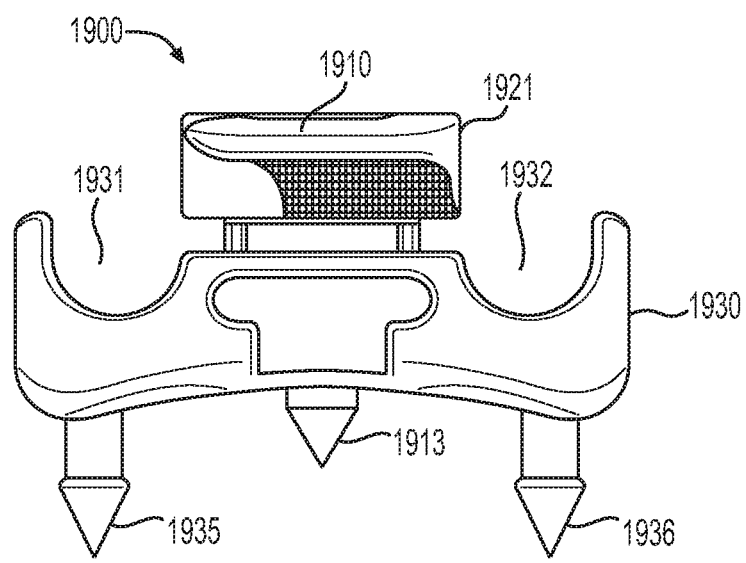
FIG. 36 is a side view of a staple stabilization system according to some embodiments of the present application.

FIG. 36 illustrates a side view of a staple stabilization system according to some embodiments of the present application. The staple stabilization system 2000 is assembled and ready to receive one or more rod members within the slots 1931 and 1932. As shown in FIG. 36, the top member 1921 is inserted into the bottom member 1930, while the set screw 2010 is received within an aperture formed through both of the members.

FIG. 37 is a top perspective view of a staple stabilization system having rod members with a top member in an "open" position, while FIG. 38 is a top perspective view of the staple stabilization system having rod members with the top member in a "closed" position, according to some embodiments of the present application. In the open configuration, the top member 1921 is oriented such that its sidewalls 1926 and 1927 do not overlap and/or obstruct the openings of the slots 1931 and 1932. As such, the staple stabilization system 2000 is capable of receiving both of the rod members 1950 and 1952 therein in the open configuration. In some embodiments, the staple stabilization system 2000 can also receive a single rod member therein. After the rod members 1950 and 1952 are received within the slots 1931 and 1932, the top member 1921 can be rotated into a "closed" configuration (shown in FIG. 38) whereby each of the sidewalls 1926 and 1927 of the top member 1921 overlay a portion of a rod member, thereby helping to secure both of the rod members within the system. In both the open and closed configurations, the staple stabilization system maintains a low profile, thereby helping to reduce the risk of injury to adjacent tissue in and around a surgical site.

FIG. 39 is a top perspective view of a bottom member of a staple stabilization system according to some embodiments of the present application. From this view, the features of the bottom member 1930 are clearly shown. For example, FIG. 39 illustrates how the slots 1931 and 1932 include textured or ridged features 1934 that serve as non-smooth surfaces to securely hold the rod members. In addition, from this figure, a ramped surface 1937 is visible on the bottom member 1930. This ramped surface 1937 advantageously helps to retain the top member 1921 in a desired orientation within the bottom member 1930 during use.

Figure 40:
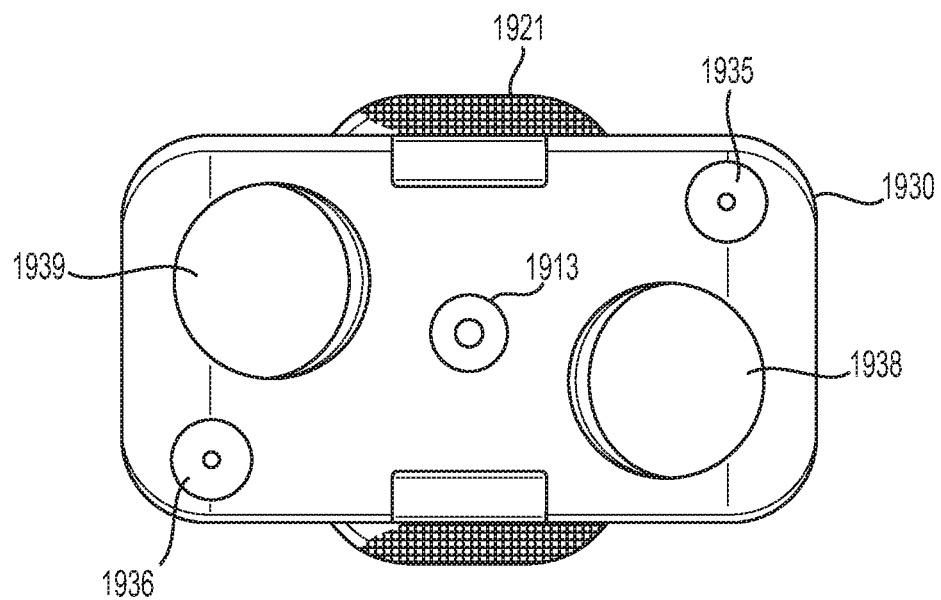
FIG. 40 is a bottom view of a staple stabilization system according to some embodiments of the present application.

FIG. 40 is a bottom view of a staple stabilization system according to some embodiments of the present application. In this view, the staple stabilization system is in an "open" configuration, whereby the top member 1921 is oriented to not obscure the slots and openings in the bottom member 1930.

FIG. 41 is a top perspective view of an alternative staple stabilizations system according to some embodiments of the present application. Unlike the staple stabilization systems disclosed in FIGS. 35-40, in which the set screw 1912 is "top-loaded" such that the threads of the set screw mate with threads on the bottom member 1930, the staple stabilization system in FIG. 41 includes a set screw 1912 that is "bottom-loaded" such that the threads of the set screw mate with threads on the top member 1921. This system advantageously provides an alternative means to secure the different components of the system in a desirable low-profile.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments.

What is claimed is:

1. A surgical method comprising:
   providing a stabilization system, wherein the stabilization system comprises:
      a bottom member in the form of a plate having a top surface and a bottom surface, the bottom member including a first opening extending from the top surface to the bottom surface and a second opening extending from the top surface to the bottom surface, wherein the bottom member includes a slot configured to receive a rod member;
      one or more protruding members extending from the bottom surface of the bottom member;
      a set screw received by the bottom member, wherein the set screw is configured to engage a vertebral body;
      a first bone screw extending through the first opening and a second bone screw extending through the second opening, the first and second bone screws configured to secure the system to a vertebral body.

2. The method of claim 1, wherein the one or more protruding members are in the form of a prong configured to engage the vertebral body.

3. The method of claim 2, wherein the prong has a pointed tip configured to engage the vertebral body.

4. The method of claim 1, further comprising securing the rod member into the stabilization system.

5. The method of claim 4, wherein the rod member is received in the bottom member.

6. The method of claim 4 wherein the set screw has a cylindrical body, and the set screw secures the rod member within the system.

7. The method of claim 6, wherein the set screw is rotated to secure the rod member within the system.

8. The method of claim 6 further comprising a top member positioned between the bottom member and the set screw.

9. A surgical method comprising:
   providing a stabilization system, wherein the stabilization system comprises:
      a bottom member having a top surface and a bottom surface, the bottom member including a first opening extending from the top surface to the bottom surface and a second opening extending from the top surface to the bottom surface;

a top member engaged with the bottom member;

a set screw received by the top member and the bottom member;

one or more protruding members extending from the bottom surface of the bottom member;

a rod member received in the bottom member; and a first bone screw extending through the first opening and a second bone screw extending through the second opening, the first and second bone screws configured to secure the system to a vertebral body,.

wherein the top member is rotatably attached to the bottom member such that when the top member is in a first position, the rod member can be received in the bottom member and when the top member is in a second position, the rod member is secured to the bottom member.

10. The method of claim 9, wherein the one or more protruding members are in the form of a prong configured to engage the vertebral body.

11. The method of claim 10, wherein the prong has a pointed tip configured to engage the vertebral body.

12. The method of claim 10, wherein the one or more protruding members include a first prong extending from a first portion of the bottom surface of the bottom member and a second prong extending from a second portion of the bottom surface of the bottom member.

13. The method of claim 9, wherein the bottom member includes a slot configured to receive the rod member.

14. The method of claim 13 wherein the set screw has a cylindrical body.

15. The method of claim 14, wherein the set screw is rotated to secure the position of the top member with respect to the bottom member.

16. A surgical method comprising:
providing a stabilization system, wherein the stabilization system comprises:
a bottom member having a top surface and a bottom surface, the bottom member including a first opening extending from the top surface to the bottom surface and a second opening extending from the top surface to the bottom surface;
a top member engaged with the bottom member;
one or more protruding members extending from the bottom surface of the bottom member;
one or more rod members received in the bottom member;
a first bone screw extending through the first opening and a second bone screw extending through the second opening, the first and second bone screws configured to secure the system to a vertebral body; and
a set screw having a cylindrical body, wherein the set screw is rotated to secure the one or more rod members within the bottom member,
wherein the set screw has a lower portion having a distal tip that extends beyond the bottom surface of the bottom member and is capable of engaging the vertebral body.

17. The method of claim 16, wherein the one or more protruding members are in the form of a prong configured to engage the vertebral body.

18. The method of claim 17, wherein the prong has a pointed tip configured to engage the vertebral body.

19. The method of claim 17, wherein the one or more protruding members include a first prong extending from a first portion of the bottom surface of the bottom member and a second prong extending from a second portion of the bottom surface of the bottom member.

* * * * *